(12) United States Patent
Surette

(10) Patent No.: US 7,195,914 B2
(45) Date of Patent: Mar. 27, 2007

(54) COMPOSITION AND METHOD FOR TREATMENT OF HYPERTRIGLYCERIDEMIA

(75) Inventor: Marc E. Surette, Winston-Salem, NC (US)

(73) Assignee: Pilot Therapeutics, Inc., Winston-Salem, NC (US)

( * ) Notice: Subject to any disclaimer, the term of this patent is extended or adjusted under 35 U.S.C. 154(b) by 0 days.

(21) Appl. No.: 10/667,529

(22) Filed: Sep. 22, 2003

(65) Prior Publication Data

US 2004/0058024 A1    Mar. 25, 2004

Related U.S. Application Data

(62) Division of application No. 09/826,437, filed on Apr. 5, 2001, now Pat. No. 6,667,064.

(60) Provisional application No. 60/228,930, filed on Aug. 30, 2000.

(51) Int. Cl.
*A61K 35/78* (2006.01)

(52) U.S. Cl. ............. 435/410; 424/776; 424/778; 510/2

(58) Field of Classification Search ........... 424/520, 424/725, 776; 510/2; 435/410
See application file for complete search history.

(56) References Cited

U.S. PATENT DOCUMENTS

| | | | |
|---|---|---|---|
| 4,999,380 A * | 3/1991 | Berger et al. ........... | 514/558 |
| 5,110,817 A | 5/1992 | Beyer | |
| 5,158,975 A | 10/1992 | Guichardant et al. | |
| 5,160,736 A | 11/1992 | Kiriyama | |
| 5,234,952 A | 8/1993 | Crozier-Willi et al. | |
| 5,502,077 A | 3/1996 | Breivik et al. | |
| 5,886,037 A * | 3/1999 | Klor et al. ............. | 514/546 |
| 6,077,828 A | 6/2000 | Abbruzzese et al. | |
| 6,171,856 B1 | 1/2001 | Thigpen et al. | |
| 6,340,485 B1 * | 1/2002 | Coupland et al. ........ | 424/776 |

FOREIGN PATENT DOCUMENTS

| WO | WO 93/19624 | 10/1993 |
|---|---|---|
| WO | WO 93/21774 | * 11/1993 |

OTHER PUBLICATIONS

Singer, P. et al., "Effects of dietary oleic, linoleic and α-linolenic acids on blood pressure, serum lipids, lipoproteins and the formation of eicosanoid precursors in patients with mild essential hypertension"; Journal of Human Hypertension, 4: 227-33 (1990).
Hokanson, J.E. et al., "Plasma triglyceride level is a risk factor for cardiovascular disease independent of high-density lipoprotein cholesterol level: a meta-analysis of population-based prospective studies"; Journal of Cardiovascular Risk, 3: 213-219 (1996).
Gotto, Jr., A.M., "Triglyceride The Forgotten Risk Factor"; Circulation, 97: 1027-1028 (1998).
Singer, P. et al., "A possible contribution of decrease in free fatty acids to low serum triglyceride levels after diets supplemented with n-6 and n-3 polyunsaturated fatty acids"; Atherosclerosis, 83: 167-175 (1990).
Harris, W.S., "Fish oils and plasma lipid and lipoprotein metabolism in humans: a critical review"; Journal of Lipid Research, 30: 785-806 (1989).
Roche, H.M., "Long-Chain n-3 Polyunsaturated Fatty Acids and Triacylglycerol Metabolism in the Postprandial State"; Lipids, 34 Suppl: S259-65 (1999).
Ishikawa, T. et al., "Effects of gammalinolenic acid on plasma lipoproteins and apolipoproteins"; Atherosclerosis, 75: 95-104 (1989).
Blum, A. et al., "Severe Gastrointestinal Bleeding Induced by a Probable Hydroxycoumarin-Bezafibrate Interaction"; Isr. Journal of Medical Science, 28: 47-49 (1992).
Abbey, M. et al., "Effect of Fish Oil on Lipoproteins, Lecithin: Cholesterol Acyltransferase, and Lipid Transfer Protein Activity in Humans"; Arteriosclerosis, 10: 85-94 (1990).
Harris, W.S. et al., "Influence of n-3 fatty acid supplementation on the endogenous activities of plasma lipases"; American Journal of Clinical Nutrition, 66: 254-60 (1997).
Abraham, R.D. et al., "Effects of safflower oil and evening primrose oil in men with a low dihomo-y-linolenic level"; Atherosclerosis, 81: 199-208 (1990).
Agren, J.J. et al., "Fish diet, fish oil and docosahexaenoic acid rich oil lower fasting and postprandial plasma lipid levels"; European Journal of Clinical Nutr., 50: 765-71 (1996).
Farmer, J.A. et al., "Antihyperlipidaemic Agents Drug Interactions of Clinical Significance"; Drug Safety, 11(5): 301-309 (1994).
Kelley, D.S. et al., "Dietary α-Linolenic Acid Alters Tissue Fatty Acid Composition, but Not Blood Lipids, Lipoproteins or Coagulation Status in Humans"; Lipids, 28: 533-537 (1993).
Harris, W.S., "n-3 Fatty Acids and Human Lipoprotein Metabolism: An Update"; Lipids, 34 Suppl: S257-8 (1999).
Weber, P., "Triglyceride-Lowering Effect of n-3 Long Chain Polyunsaturated Fatty Acid: Eicosapentaenoic Acid vs. Docosahexaenoic Acid"; Lipids, 34 Suppl: S269 (1999).
Wu, D. et al., "Effect of dietary supplementation with black currant seed oil on the immune response of healthy elderly subjects"; Am. J. Clinical Nutrition, 70: 536-43 (1999).
Diboune, M. et al., "Composition of Phospholipid Fatty Acids in Red Blood Cell Membranes of Patients in Intensive Care Units: Effects of Different Intakes of Soybean Oil, Medium-Chain Triglycerides, and Black-Currant Seed Oil"; Journal of Parenteral and Enteral Nutrition, 16(2): 136-41 (1992).

(Continued)

Primary Examiner—Ruth A. Davis
(74) Attorney, Agent, or Firm—Dann, Dorfman, Herrell and Skillman, P.C.; Patrick J. Hagan

(57) ABSTRACT

A polyunsaturated fatty acid-containing composition for treating hypertriglyceridemia and methods of use thereof are provided.

7 Claims, No Drawings

OTHER PUBLICATIONS

Diboune, M.D. et al., "Soybean Oil, Blackcurrant Seed Oil, Medium-Chain Triglycerides, and Plasma Phospholipid Fatty Acids of Stressed Patients"; Nutrition, 9(4): 344-49 (1993).

Viikari, J. et al., "Effect of primrose oil on serum lipids and blood pressure in hyperlipidemic subjects"; International Journal of Clinical Pharmacology, Therapy and Toxicology, 24(12): 668-670 (1986).

Chaintreuil, J. et al., "Effects of Dietary γ-Linolenate Supplementation on Serum Lipids and Platelet Function in Insulin-Dependent Diabetic Patients"; Human Nutrition: Clinical Nutrition, 38C: 121-130 (1984).

Guivernau, M. et al., "Clinical and Experimental Study on the Long-term Effect of Dietary Gamma-linolenic Acid on Plasma Lipids, Platelet Aggregation, Thromboxane Formation, and Prostacyclin Production"; Prostaglandins Leukotrienes and Essential Fatty Acids, 51: 311-6 (1994).

\* cited by examiner

COMPOSITION AND METHOD FOR TREATMENT OF HYPERTRIGLYCERIDEMIA

This application is a divisional of U.S. patent application Ser. No. 09/826,437, filed on Apr. 5, 2001 now U.S. Pat. No. 6,667,064, which claims the benefit of U.S. Provisional application No. 60/228,930 filed on Aug. 30, 2000. The entire disclosure of each of the aforementioned applications is incorporated herein by reference.

FIELD OF THE INVENTION

The present invention relates to a polyunsaturated fatty acid-containing composition which may be formulated as a dietary supplement or a pharmaceutical preparation, and to the use of such composition for treating hypertriglyceridemia.

BACKGROUND OF THE INVENTION

Several publications are referenced in this application by author name and year of journal publication in parentheses in order to more fully describe the state of the art to which this invention pertains. Full citations for these references are found at the end of the specification. The disclosure of each of these publications is incorporated by reference herein.

It is known that hyperlipidemia is a significant risk factor in the development of cardiovascular disease (CVD). Hyperlipidemia is a condition marked by an increase in serum levels of one or both of serum cholesterol and neutral fats, primarily triglycerides (TG). Research conducted over the last several decades has established that elevated serum TG levels constitute an independent risk factor for CVD. Accordingly, the development of agents for reducing or controlling serum TG levels has received considerable attention as a means of preventing or delaying the onset of CVD.

As a dietary treatment for hypertriglyceridemia, polyunsaturated fatty acids (PUFAs) have been recommended, in conjunction with limited caloric intake. In this connection, dietary marine oils have been shown to exhibit very potent hypotriglyceridemic (TG lowering) properties, especially in type V hypertriglyceridemic individuals (Roche, 1999; Harris 1999; Harris 1989).

Numerous studies have now shown that the daily consumption of fish oils containing as little as 2–4 grams of n-3 PUFAs can significantly decrease circulating TG levels in both normolipidemic and hypertriglyceridemic individuals (Harris 1989; Harris 1997). Although there has been some question regarding the constituent(s) of dietary marine oils that is (are) responsible for this hypotriglyceridemic effect, both eicosapentaenoic acid (20:5 n-3) (EPA) and docosahexaenoic acid (22:6 n-3) (DHA), which are major constituents of fish oils, have been shown to possess this hypotriglyceridemic activity in humans (Weber 1999; Agren, 1996). However, this effect is not a general attribute of the n-3 PUFAs, as oils containing dietary alpha-linolenic acid (18:3 n-3) (ALA), a precursor of EPA and DHA, have little if any hypotriglyceridemic activity even when consumed in oils delivering as much as 20 grams of ALA per day (Kelley 1993; Abbey, 1990). A hypotriglyceridemic effect has been reported for ALA-containing oils when consumed at extremely elevated concentrations (40–60 grams ALA/day) (Singer, 1990), but this effect compares poorly to that of dietary marine oils and may be a generalized effect of high doses of dietary PUFAs, since high doses of linoleic acid have similar properties. However, the dietary use of marine oils as hypotriglyceridemic agents is undesirable for many individuals due to their generally unpleasant taste and odor. Furthermore, many studies investigating the potential benefits of marine oil consumption report associated gastrointestinal problems such as bloating and gas.

There have been few reports on studies in humans to determine the extent to which consumption of stearidonic acid (SDA) influence in vivo conversion to longer chain fatty acids, i.e., Arachidonic acid and Docosapentaenoic acid (DPA). Those that have been published appear inconclusive. For example, no increase in longer chain n-3 fatty acids was seen in test subjects who consumed the daily dose of 0.65 g ALA and 0.17 g SDA (Wu, 1999). Intensive care unit patients who were administered the equivalent of 5.7 g ALA and 0.7 g SDA per day were found to have a 20% increase in the EPA content of red blood cell membranes that was statistically significant (Diboune, 1992). Measurement of plasma fatty acids in a similar group of patients showed a significant increase in DPA; however, there is no mention of the plasma content of the of EPA (Diboune, 1993).

Another fatty acid that can be found in some less common dietary-oils is gamma-linolenic acid (18:3 n-6) (GLA). Although oils containing GLA, such as Borage oil and Evening Primrose oil (EPO), have been extensively studied for their anti-inflammatory benefits, very little information exists regarding their effects on circulating TG levels. Five studies have been reported in humans in which circulating TGs were monitored following the consumption of oils containing GLA. In all five studies, human diets were supplemented with EPO. Three of the studies showed no effect of the supplementation on circulating TG levels in subjects consuming 0.3 grams, 0.6 grams and 2.7 grams of GLA per day for up to 4 months (Ishikawa, 1989; Abraham, 1990; Viikari 1986). The Abraham study (2.7 grams/day) utilized healthy males without signs of hyperlipidemia, but who were selected based on their being in the lowest quintile for GLA content in adipose tissue biopsies from a larger group of subjects. The Ishikawa study (0.3 grams GLA/day) involved 19 hypercholesterolemic patients. Ten patients did not have associated hypertriglyceridemia and nine were considered hypertriglyceridemic based on a cut off of 150 mg/dl. The Viikari study (0.6 grams GLA/day) utilized hyperlipidemic patients. The two other studies reported chat diets supplemented with EPO, delivering either 0.24 grams GLA/day or 2 grams GLA/day, significantly decreased circulating TG levels by 48% and 35%, respectively (Guivernau, 1994; Chaintreuil, 1984). In the Chaintreuil study, all subjects were diabetics taking daily subcutaneous insulin injections. The subjects were grouped to receive either 2 grams GLA/day or 0.5 grams GLA/day. The 2.0 grams/day group were found to have a decrease in plasma TG of 35% while the 0.5 grams/day showed no change in TG levels. The Guivernau paper studied 12 hyperlipidemic men who received 0.24 grams GLA/day. These men had combined hyperlipidemia and any subjects who were taking lipid lowering drugs discontinued the treatment at least 8 weeks before the start of the study. The oil supplement was reported to cause a 48% decrease in plasma TG within a 4 week period, and those individuals with the highest initial levels showed the most marked decrease.

While EPO and Borage Oil are distinctive, in part, because they contain GLA, there have been no reported studies to date which have addressed whether GLA is the active component responsible for the hypotriglyceridemic effects reported in the last-mentioned two studies. Therefore, in view of the inconsistent reports in the literature and the absence of studies addressing whether GLA itself may possess hypotriglyceridemic activity, there is at this time no conclusive evidence to indicate that dietary GLA possesses hypotriglyceridemic properties.

Known pharmaceutical agents for treating hypertriglyceridemia include the class of fibrate drugs, e.g., clofibrate, benzafibrate and gemfibrozil, as well as nicotinic acid and derivatives thereof. Nicotinic acid has been shown to be safe and effective for lowering serum TG levels, but the therapeutic dosage must be worked up to gradually to minimize the flushing and itching of skin which frequently cannot be tolerated by the patient. Clinically relevant interactions of fibrates with other anti-hyperlipidemic drugs include rhabdomyolysis when used in combination with HMG CoA-reductase inhibitors (statins), and decreased bioavailability when combined with certain bile acid sequesterants (Farmer and Gotto, 1994). Also, potentiation of the anticoagulant effects of coumarin may cause bleeding (Blum, 1992).

From the foregoing summary, it will be appreciated that a need exists for a composition for treating hypertriglyceridemia that is both effective and well tolerated by patients to whom it is administrated.

SUMMARY OF THE INVENTION

In accordance with one aspect, the present invention provides a composition comprising a mixture of fatty acyl compounds having a polyunsaturated fatty acid content of at least 65 weight percent and including linoleic acid in an amount from about 10 to about 35 weight percent, γ-linolenic acid, in an amount from about 5 to about 50 weight percent, α-linolenic acid, in an amount from about 15 to about 60 weight percent and stearidonic acid, in an amount from about 15 to about 55 weight percent, the stated amounts being based on the total weight of the polyunsaturated fatty acid content of the fatty acyl compound mixture, and at least one therapeutic agent selected from, the group of antilipemic agents, antioxidants and anti-diabetic agents.

In accordance with another aspect, the present invention provides a method of using the fatty acyl compound mixture described above, with or without the therapeutic agent, for the treatment of hypertriglyceridemia in patients in need of such treatment.

DETAILED DESCRIPTION OF THE INVENTION

The fatty acyl compound-containing mixture used in the practice of this invention may be formulated from individual fatty acyl compounds, or derived as such from is a natural source. As used herein, the expression "fatty acyl compound" refers to various forms of fatty acids, including without limitation, free acids, simple esters, diglycerides, triglycerides, phospholipids, and the like. Phospholipids include, without limitation, lecithins, other fatty acid derivatives of phosphatidic acid, sphingomyelin and plasmalogens. The polyunsaturated fatty acid content of the fatty acyl-compound mixture is determined on the basis of the relative amounts of free acid, when present as such in the mixture, or free acid produced upon hydrolysis of acid derivatives such as esters, di- or triglycerides and phospholipids.

The fatty acyl compound-containing component of the composition is preferably obtained from the seeds of the genus Echium, e.g., Echium plantagineum and Echium vulgaris (hereinafter referred to as Echium oil).

Echium, oil contains a unique fatty acyl composition, which upon oral administration to humans results in a significant decrease in circulating triglyceride levels in both normolipidemic as well as in hypotriglyceridemic individuals. Furthermore, for those having predisposition to hypertriglyceridemia, the ingestion of Echium oil reduces the serum level of neutral fat through a daily diet to delay the onset of hypertriglyceridemia.

Echium oil contains important quantities (>10% each) of four different polyunsaturated fatty acids as set forth in Table 1 below.

TABLE 1

FATTY ACYL COMPOSITION (% BY WEIGHT) OF SEED OIL FROM ECHIUM PLANTAGENEUM AND ECHIUM VULGARIS.

| Fatty Acid | Amount E. Plantageneum | Amount E. Vulgaris |
|---|---|---|
| Palmitic acid 16:0 | 7.1 | 6.2 |
| Stearic acid 18:0 | 3.7 | 2.0 |
| Oleic acid 18:1n-9 | 15.8 | 8.0 |
| Linoleic acid 18:2n-6 | 14.3 | 10.3 |
| γ-Linolenic acid 18:3n-6 | 11.2 | 5.3 |
| α-Linolenic acid 18:3n-3 | 33.1 | 47.3 |
| Stearidonic acid 18:4n-3 | 13.9 | 19.8 |
| Others | 0.9 | 1.1 |

Most preferred is the oil obtained from E. Plantagineum, which contains approximately equivalent amounts of GLA, linoleic acid and SDA. Echium oil also has elevated concentrations of ALA (more than double to triple that of other PUFAs). Both ALA and SDA are 18 carbon chain precursors of the long chain n-3 fatty acids found in marine oils.

Oil from E. Plantagineum is commercially available from Croda International PLC of Great Britain. A commercial product can be obtained which is the basic seed extract, having the composition set forth in Table 1 above. Alternatively, a concentrated form of Echium oil may be used, if desired.

As can be seen from the above table, Echium oil also has saturated fatty acid and mono-unsaturated fatty acid components, which predominantly comprise $C_{16}$ and $C_{18}$ fatty acids.

There is no other natural oil known which contains the profile of polyunsaturated fatty acids found in Echium oil. Table 2 shows the fatty acyl compositions of the commercially-available oils which most closely approach that of Echium oil.

TABLE 2

FATTY ACYL COMPOSITIONS OF COMMERCIALLY-AVAILABLE OILS

| | | Percent of fatty acids | | |
|---|---|---|---|---|
| Fatty Acid | | Evening Primrose Oil | Borage Oil | Black Currant Oil |
| Palmitic acid | 16:0 | 5 | 11 | 6 |
| Stearic acid | 18:0 | 2 | 4 | 2 |
| Oleic acid | 18:1n-9 | 10 | 18 | 14 |
| Linoleic acid (PUFA) | 18:2n-6 | 74 | 40 | 48 |
| Gamma-linolenic acid (PUFA) | 18:3n-6 | 9 | 20 | 19 |
| Alpha linolenic acid (PUFA) | 18:3n-3 | — | <1 | 14 |
| Stearidonic acid (PUFA) | 18:4n-3 | — | — | 2.5–4 |
| Other | | — | 7 | — |

One of the unusual characteristics of Echium oil is its elevated content of SDA. Black current oil, which has an SDA content of about 4% of the total fatty acids, is the only dietary oil which is anywhere near having the SDA content of *Echium* oil. SDA is a product of the desaturation of ALA. This desaturation step, which inserts a double bond in the carbon chain, is one of 3 steps required for the conversion of ALA to EPA (which is found in marine oils), as represented below.

Like ALA, dietary SDA can be converted in tissues to EPA. However, it is not apparent that dietary SDA itself or the conversion of SDA to EPA in tissues will necessarily result in a hypotriglyceridemic effect. Indeed, although individuals who consume ALA show a small increase in tissue levels of EPA, the consumption of up to 20 grams of ALA per day does not result in a lowering of circulating TG levels.

While not wishing to be bound to a particular theory, it is believed that the hypotriglyceridemic effect of dietary *Echium* oil is likely due to the unique combination of linoleic, GLA, ALA and SDA found in this oil, rather than the individual effect of any one fatty acid component of the oil.

The fatty acyl compound mixture described herein may be used as a complete food product, as a component of a food product, as a dietary supplement or as part of a dietary supplement and may be in either liquid, semi-solid or solid form. For example, the fatty acyl compound mixture may be administered as a tablet, a gelatin capsule, a flavored drink, a powder that can be reconstituted into such a drink, a cooking oil, salad oil or dressing, sauce, syrup, mayonnaise, margarine or the like. Preferably, the fatty acyl compound mixture is in the form of a flavored emulsion that can be consumed neat or easily mixed in a drink or yogurt.

The composition of the invention is beneficially administered so as to deliver from about 0.04 to about 0.35 grams of the fatty acyl compound mixture per kilogram of patient body weight per day.

The fatty acyl compound mixture, if desired, may be administered either simultaneously or sequentially in combination with one or more therapeutic agent which has antilipemic, antioxidant or antidiabetic activity. Representative examples of useful of antilipemic agents are nicotinic acid, fluvastatin sodium, cerivastatin sodium, simvastatin, atorvastatin calcium, lovastatin, clofibrate, ciprofibrate, gemfibrozil, benzafibrate, fenofibrate and pravastatin sodium.

Nicotinic acid (niacin) acts by decreasing circulating TGs. The fibrate drugs decrease circulating TGs and LDL-cholesterol. The various statins referred to above block cholesterol synthesis and promote the uptake of LDL-cholesterol by the liver due to an up-regulation of the hepatic LDL receptor. The overall effect produced is a decrease in circulating LDL-cholesterol concentration.

Suitable antioxidants include tocopherol, ascorbic acid, tocotrienol, selenium, curcumin, β-carotene and probucol. These compounds are anti-atherogenic, as they limit the formation of atherogenic oxidized lipoproteins. Antioxidants such as tocopherol, ascorbyl palmitate, ascorbic acid and lecithin or a mixture of such antioxidants also serve to protect the composition against oxidation.

Among the antidiabetic agents which may be incorporated in the composition of this invention are troglitazone, pioglitazone, rosiglitazone and metformin. The glitazone drugs reduce plasma TG, glucose and insulin levels in patients with non-insulin-dependent diabetes mellitus. Metformin lowers moderate (non-diabetic) fasting hypertriglyceridemia in individuals at risk for Type II diabetes.

The composition of the invention may be administered enterally, with oral administration being the preferred route.

Compositions intended for oral administration may be prepared according to any known method for the manufacture of dietary supplements or pharmaceutical preparations, and such compositions may include at least one additive selected from the group consisting of taste improving substances, such as sweetening agents or flavoring agents, stabilizers, emulsifiers, coloring agents and preserving agents in order to provide a dietetically or pharmaceutically palatable preparation. Vitamins, minerals and trace element from any physiologically acceptable source may also be included in the composition of the invention.

In compositions including the above-mentioned therapeutic agents, the dosage and route of administration should be in accordance with the manufacturer's instructions.

The following examples are provided to illustrate certain embodiments of the invention. They are not intended to limit the invention in any way.

EXAMPLE I

Hypotriglyceridemic Properties of *Echium* Oil

A preferred composition is a stabilized emulsion that can be consumed neat or easily mixed in a drink or yogurt. An example of such a composition is the following:

| Constituents | Total Weight (g) |
|---|---|
| Purified water | 49.28 g |
| Ascorbyl palmitate | 0.2 g |
| Sorbic acid | 0.16 g |
| Sucrose | 5 g |
| Glycerin | 5 g |
| Xanthan gum | 0.4 g |
| Echium Plantagineum Seed Oil | 35 g |
| Atorvastatin | 0.01 g |
| Flavor (fruit flavored) | 5 g |
| Colorant | 0.05 g |
| | 100 g |

The composition is conveniently packaged in an oxygen-free environment in single daily dosage containers made of oxygen impermeable materials such as foil-lined pouches. The recommended daily dosage would be approximately 40 g per day, thus providing a dose of about 15 g of *Echium* oil per day.

EXAMPLE II

A single-center, open label pilot study was carried out in which 15 g of echium plantagineum oil was administered per day to healthy subjects with mild to moderate hypertriglyceridemia. The study involved a 4-week diet lead-in period, followed by a 4-week treatment period. Approximately 20 subjects were enrolled in order to randomize 11 subjects.

Potential subjects underwent a screening visit (Week-4) where medical history and medication use were evaluated and vital signs and serum lipid profiles were obtained. Diet recall was also obtained and diet instruction provided. Subjects with serum triglyceride levels of over 300 mg/dl at the screening visit were enrolled in the study and asked to return 2 weeks later (Week-2) and again 2 weeks after that (Week 0, Baseline), provided they satisfied the following inclusion criteria. The subjects must have been either male or non-pregnant female. The subjects must have been 20 years of age or older, must not have had significant medical conditions that would preclude the subject's participation in the study, and they must have signed an informed consent. The subject's weight must have been within 2 kg from Screening Visit to Baseline Visit, and the subjects must have been willing to follow all study procedures including study visits, fasting blood draws, normal eating habits, and compliance with study supplement dosage of five capsules three times a day. Subjects also had to have an LDL-cholesterol level <160 mg/dl and triglyceride levels between 300–450 mg/dl, based on an average of lipid results at the Week-2 Visit and the Baseline Visit.

Subjects were excluded from participation in the study for any of the following criteria: The subjects were pregnant or breast feeding women. The subjects had medical conditions such as active peptic ulcer, inflammatory bowel disease, gastrointestinal bleeding or any medical condition or prior gastrointestinal surgery that could influence absorption, metabolism or excretion of the study supplement, angina, arrhythmia, congestive heart failure or history of myocardial infarction or stroke, or insulin-dependent diabetes (Type 1 or Type 2). Subjects were also excluded from the study if they had a history of or were currently taking any cholesterol-reducing products, ingredients or fibers for 30 days prior to screening.

Subjects who met the inclusion and exclusion criteria at the Screening Visit and who gave their written informed consent underwent the following investigations:

At the Week-2 Visit (Visit 2), the following procedures were performed: adverse event assessment, concomitant medication assessment (including all vitamins and supplements), diet recall, diet instruction, blood pressure, heart rate, weight, fasting blood lipid profile and a fatty acid profile. Additionally, subjects were instructed to maintain their current diets, medications, vitamin supplements and usual physical activities throughout the study. Subjects were then scheduled to return to the research center after approximately 2 weeks plus or minus 2 days for the Week-0 Baseline Visit.

At the Week-0 Baseline Visit (Visit 3), the following procedures were performed: Adverse event assessment, concomitant medication assessment, blood pressure, heart rate, weight, fasting blood lipid profile, chemistry panel and urine pregnancy test, if applicable. Subjects were also dispensed Echium oil capsules and were instructed to take fifteen (15) capsules a day, 5 with each of their 3 daily meals, for a total daily dose of 15 grams of Echium oil per day. The subjects were further instructed to take these capsules with meals. Additionally, the subjects were instructed to maintain their current diets, medications, vitamin supplements, and usual physical activities throughout the study. Subjects were then scheduled to return to the research center after approximately 26 days plus or minus one day for the Day 26 Visit.

At the Day 26 Visit (Visit 4), the subjects visited the research center only for a fasting lipid profile. The subjects were then scheduled to return to the research center on Day 28 plus or minus one day for the Week 4 (Visit 5/Final Visit).

At the Week 4 Visit (Visit 5/Final Visit), the following procedures were performed: Adverse event assessment, concomitant medication assessment, blood pressure, heart rate, weight, fasting blood lipid profile, chemistry panel, urine pregnancy test, if applicable and assessment of product compliance. Any unused Echium capsules were returned. The results of the study on 11 subjects are presented in Table 3.

TABLE 3

Values are plasma triglycerides in mg/dL.

| Patient | Baseline Visit 3 | Visit | Visit 5 | Average of Visits 4 and 5 | % Decrease (Visits 4 + 5/Visit 3) |
|---|---|---|---|---|---|
| 1 | 358 | 237 | 309 | 273 | 23.7 |
| 2 | 420 | 313 | 335 | 324 | 22.9 |
| 3 | 330 | 377 | 274 | 326 | 1.4 |
| 4 | 527 | 332 | 460 | 396 | 24.9 |
| 5 | 382 | 208 | 161 | 185 | 51.2 |
| 6 | 296 | 231 | 205 | 218 | 26.4 |
| 7 | 424 | 472 | 460 | 466 | −9.9 |
| 8 | 352 | 238 | 221 | 230 | 34.8 |
| 9 | 312 | 232 | 209 | 221 | 29.3 |
| 10 | 262 | 250 | 268 | 259 | 1.1 |
| 11 | 320 | 261 | 298 | 280 | 12.7 |

The results presented in Table 3 indicate that intake of 15 g/day of Echium oil had a hypotriglyceridemic effect on 8 out of 11 subjects. The subjects consumed 15 g/day of Echium oil for 4 weeks. Of the eleven subjects listed in Table 3, one had a decrease in triglycerides of approximately 13%, four had decreases of about 25%, one had a decrease of approximately 30%, one had a decrease of approximately 35% and one had a decrease of approximately 52%. Only 3 subjects had little reduction or an increase in triglyceride levels. The overall mean decrease was 20% and was 28.3% amongst the 8 subjects who responded to the treatment.

REFERENCES

1. Abbey M, et al., Arteriosclerosis, 10:85–94 (1990).
2. Abraham R D, et al., Atherosclerosis, 81:199–208 (1990).
3. Agren J J, et al., European Journal of Clinical Nutr., 50:765–71 (1996).
4. Blum, A, et al., Isr. Journal of Medical Science, 28(1):47–49 (1992).
5. Chaintreuil J, et al., Human Nutrition and Clinical Nutrition, 38:121–30 (1984).
6. Diboune et al., Nutrition, 9:433–49 (1993).
7. Diboune et al., parenteral & enteral nutrition, 16:136–41 (1992).
8. Gotto, A M, Circulation, 97: 1027–1028 (1998).
9. Guivernau M, et al., Prostaglandins Leukotrienes and Essential Fatty Acids, 51:311–6 (1994).
10. Farmer, J and Gotto, A M, Drug Safety, 11(5):307–309 (1994).
11. Harris W S, Journal of Lipid Research, 30:785–807 (1989).
12. Harris W S, American Journal of Clinical Nutrition, 66:254–60 (1997).
13. Harris W S, Lipids, 34 Suppl:S257–8 (1999).
14. Hokanson J E and Austin M A., Journal of Cardiovascular Risk, 3:213–219 (1996).
15. Ishikawa T, et al., Atherosclerosis, 75:95–104 (1989).
16. Kelley D S, et al., Lipids. 28:533–537 (1993).
17. Roche H M and Gibney M J, Lipids. 34 Suppl:S259–65 (1999).
18. Singer P, et al., Journal of Human Hypertension, 4:227–33 (1990).
19. Viikari J and Lehtonen A, International Journal of Clinical Pharmacology Therapeutics and Toxicology, 24:668–70 (1986).
20. Weber P, Lipids, 34 Suppl:S269 (1999).
21. Wu et al., Am. J. Clinical Nutrition, 70: 536–43 (1999).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating hypertriglyceridemia in a patient in need of such treatment, said method comprising administering to said patient a therapeutically effective amount of a composition comprising a mixture of fatty acyl compounds, said fatty acyl compound mixture having a polyunsaturated fatty acid content of at least 65 weight percent and including linoleic acid in an amount from about 10 to about 35 weight percent, γ-linolenic acid in an amount from about 5 to about 50 weight percent, α-linolenic acid in an amount from about 15 to about 60 weight percent and stearidonic acid in an amount from about 15 to about 55 weight percent, said amount being based on the total weight of the polyunsaturated fatty acid content of said mixture, optionally, in combination with at least one therapeutic agent selected from the group of antilipemic agents, antioxidants and antidiabetic agents.

2. A method according to claim 1, wherein said composition is administered in an amount which delivers from about 0.04 to about 0.35 grams of said fatty acyl compound mixture per kilogram of patient body weight per day.

3. A method according to claim 1, wherein said composition is administered orally.

4. A method as claimed in claim 1, wherein said composition is administered as a single dose.

5. A method according to claim 4, wherein said single dose comprises *Echium* oil.

6. A method according to claim 5, wherein said composition is administered in an amount which delivers about 15 grams of *Echium* oil per day.

7. A method as claimed in claim 5, wherein the polyunsaturated fraction of said *Echium* oil is concentrated.

* * * * *